(12) United States Patent
Pelletier et al.

(10) Patent No.: US 6,187,325 B1
(45) Date of Patent: Feb. 13, 2001

(54) USE OF AT LEAST ONE EXTRACT OF A ROSACEA OF THE GENUS SANGUISORBA OFFICINALIS FOR PROMOTING PIGMENTATION OF THE SKIN AND/OR THE BODY HAIR AND/OR THE CRANIAL HAIR

(75) Inventors: Pascale Pelletier, Antony; Marcelle Regnier, Paris, both of (FR)

(73) Assignee: L'Oreal, Paris (FR)

( * ) Notice: Under 35 U.S.C. 154(b), the term of this patent shall be extended for 0 days.

(21) Appl. No.: 09/377,858

(22) Filed: Aug. 20, 1999

(30) Foreign Application Priority Data

Sep. 7, 1998 (FR) .................................. 98 11154

(51) Int. Cl.$^7$ .............................. A61K 7/00; A61K 7/42; A61K 7/06; A61K 35/78; A61K 47/00
(52) U.S. Cl. .............................. 424/401; 424/59; 424/74; 424/195.1; 514/783
(58) Field of Search ............................... 424/401, 59, 74, 424/195.1; 514/783

(56) References Cited

U.S. PATENT DOCUMENTS 5,567,419 * 10/1996 Togiya et al. ........................... 424/74
5,766,614 * 6/1998 Yong ..................................... 424/401

FOREIGN PATENT DOCUMENTS

| 1104509 | * | 7/1995 | (CA) . |
| 0 375 082 | | 6/1990 | (EP) . |
| 0 727 217 | | 8/1996 | (EP) . |
| 63-303910 | * | 12/1988 | (JP) . |
| 03188008 | * | 8/1991 | (JP) . |
| 03188014 | * | 8/1991 | (JP) . |
| 04069324 | * | 3/1992 | (JP) . |
| 08268837 | * | 10/1996 | (JP) . |
| 10158181 | * | 6/1998 | (JP) . |
| 11012122 | * | 1/1999 | (JP) . |
| 11029460 | * | 2/1999 | (JP) . |

OTHER PUBLICATIONS

Shinomiya Tatsura, Patent Abstracts of Japan, Publication No. 63303910, Publication Date Dec. 12, 1988, vol. 013, No. 137 (C–582).

* cited by examiner

Primary Examiner—Shelley A. Dodson
Assistant Examiner—Marina Lamm
(74) Attorney, Agent, or Firm—Oblon, Spivak, McClelland, Maier & Neustadt, P.C.

(57) ABSTRACT

A cosmetic or dermatological composition, comprising at least one extract of a rosacea of the genus Sanguisorba in a quantity of approximately 0.002% to approximately 10% by weight, based on the total weight of said composition.

10 Claims, No Drawings

USE OF AT LEAST ONE EXTRACT OF A ROSACEA OF THE GENUS SANGUISORBA OFFICINALIS FOR PROMOTING PIGMENTATION OF THE SKIN AND/OR THE BODY HAIR AND/OR THE CRANIAL HAIR

BACKGROUND OF THE INVENTION

Field of the Invention

The present invention relates to the use of at least one extract of a rosacea of the genus Sanguisorba in a cosmetic composition and/or for producing a dermatological composition, with the extract and/or the composition being intended for promoting pigmentation of the skin and/or the body hair and/or the cranial hair, as well as to the use of at least one extract of a rosacea of the genus Sanguisorba as a propigmentation agent and/or simulator of melanogenesis in a cosmetic composition and/or for producing a dermatological composition. The present invention also relates to a cosmetic process for pigmenting the skin and/or the body hair and/or the cranial hair, which process consists in applying, to the skin and/or the body hair and/or the cranial hair, a composition which comprises at least one extract of a rosacea of the genus Sanguisorba.

The color of the cranial hair and the human skin depends on a variety of factors, which, in particular, include the seasons of the year, and the race, sex and age of the individual. Color is principally determined by the concentration in the keratinocytes of melanin, which is produced by the melanocytes. The melanocytes are specialized cells which synthesize melanin using special organelles, i.e. the melanosomes.

The synthesis of melanin, or melanogenesis, is particularly complex and, in outline, involves the following main steps:

Tyrosine→Dopa→Dopaquinone→Dopachrome→Melanin

Tyrosinase (monophenoldihydroxylphenylalanine:oxygen oxidoreductase/EC 1.14.18.1) is the essential enzyme involved in this sequence of reactions. In particular, the enzyme catalyzses the reaction in which tyrosine is transformed into dopa (dihydroxyphenylalanine) and the reaction in which dopa is transformed into dopaquinone.

In the epidermis, the melanocyte is involved in the epidermal melanic unit, which consists of one melanocyte surrounded by approximately 36 neighboring keratinocytes. All individuals, irrespective of phototype, possess approximately the same number of melanocytes in a given area of skin. Ethnic differences in terms of pigmentation are not due to the number of melanocytes but, instead, to the properties of their melanosomes. The melanosomes are aggregated into complexes and are of small size. They are highly specialized organelles whose sole function is to produce melanin. They arise from the endoplasmic reticulum in the form of spherical vacuoles termed premelanosomes. While the premelanosomes contain an amorphous protein substrate, they do not contain any melanogenic enzymes. During maturation of the premelanosome, the amorphous substrate organizes itself into an orientated fibrillar structure along the longitudinal axis of the melanosome. Four stages are distinguished in the development of the melanosome, corresponding to the intensity of the melanization. The melanin is deposited uniformly on the internal fibrillar network of the melanosome, and the opacity of the organelle increases until saturation is reached. As the melanin is synthesized in the melanosomes, the latter move from the perinuclear region towards the ends of the dendrites of the melanocytes. The ends of the dendrites are captured by the keratinocytes, by means of phagocytosis, after which the membranes are degraded and the melanosomes are redistributed in the keratinocytes.

Although the level of melanin varies from one population to another, the quantity of tyrosinase does not vary significantly, and the level of tyrosinase messenger RNAs is identical in white and black skins. The variations in melanogenesis are, therefore, are caused by variations either in the activity of the tyrosinase or in the ability of the keratinocytes to phagocytose the melanosomes.

It is known that, in most populations, obtaining a brown skin color and maintaining a constant cranial hair color are important aspirations.

Furthermore, diseases of the pigmentation exist, such as vitiligo, which is an autoimmune disease which is characterized by the appearance on the skin of white patches which are linked to a defect of pigmentation.

There is, therefore, a genuine need for a product which facilitates and/or improves the pigmentation of the skin and/or of the body hair and/or of the cranial hair.

Numerous solutions have been proposed within the sphere of artificial coloration, involving the provision of exogenous dyes such as DHA, which are supposed to impart to the skin and/or the body hair and/or the cranial hair a color which is as close as possible to the natural color, or in the sphere of natural coloration, involving stimulation of the natural pathways of pigmentation, for example by using active compounds which stimulate melanogenesis with or without the action of UV light such as αMSH or prostaglandins. For example, publications WO-A-9517161, WO-9511003, WO-A-9501773, WO-A-9404674, WO-A-9404122, EPA-585018, WO-A-9310804, WO-A-9220322 and WO-A-9107945 have proposed solutions which are as varied as compositions which contain a phosphodiesterase inhibitor, and the use of prostaglandins, of DNA fragments and of tyrosine derivatives.

While excellent results have certainly been obtained using the solutions which have been proposed in the prior art, the compounds employed either frequently exhibit significant side-effects or are complex mixtures which lack specificity.

SUMMARY OF THE INVENTION

Accordingly, one object of the present invention is to provide a composition which affects the pigmentation of the skin, the body hair and/or the cranial hair without exhibiting the troublesome side-effects of conventional compositions.

Briefly, this object and other objects of the present invention as hereinafter will become more readily apparent can be attained by a cosmetic or dermatological composition, comprising: at least one extract of a rosacea of the genus Sanguisorba in a quantity of approximately 0.002% to approximately 10% by weight, based on the total weight of the composition.

Another aspect of the invention is a method of promoting pigmentation of the skin, the body hair and/or the cranial hair, by applying to the skin, body hair and/or cranial hair a cosmetic and/or dermatological composition comprising at least one extract of a rosacea of the genus Sanguisorba.

DETAILED DESCRIPTION OF THE PREFERRED EMBODIMENTS

It has now been discovered that, surprisingly, an extract of a rosacea of the genus Sanguisorba, preferably of the species Sanguisorba officinalis, has an activating effect, even at low concentrations, on melanogenesis, without exhibiting any cytotoxicity. This extract makes it possible to obtain natural and deep coloration of the skin, the body hair and/or the cranial hair, as well as protection from UV light, unlike dyes of the exogenous type.

Sanguisorba officinalis is a herbaceous plant of temperate regions, which is also called great burnet and which belongs to the Rosaceae family. The root of Sanguisorba officinalis mainly consists of phenolic compounds and triterpene glycosides. Those phenolic compounds are caffeic acid and chlorogenic acid, simple coumarins and furocoumarins, but especially tannins and, in particular, ellagitannins, as well as catechols and gallocatechols. Sanguisorba officinalis also contains organic acids (quinic and tiglic acids) and an essential oil containing terpenoids.

The composition of the Sanguisorba officinalis root justifies its use in traditional Chinese medicine as a hemostatic, antiseptic and anti-inflammatory agent, in particular for use against haemorrhoidal and uterine haemorrhages and as an astringent in the treatment of burns and eczema. The use of Sanguisorba officinalis in anti-ageing cosmetic preparations, on account of its anti-free radical and anti-oxidizing properties, has also been proposed.

Other compositions for topical application to the skin have also been described in EP 0 375 082, JP 03-258711 and JP 63-303910. More specifically, EP 0 375 082 discloses a composition which contains an extract of Sanguisorba officinalis rhizome and a phosphatide of the monoacyl type, which composition can be used, for example, in the form of a cream for controlling acne or on the form of a hair lotion. Japanese Patent specification JP 03-258711 discloses the use of an extract of Sanguisorba officinalis root to obtain a pentagalloylglucose, which is intended for clarifying the skin. Another clarifying composition containing an extract of Sanguisorba officinalis is disclosed in Japanese Patent specification JP 63-303910, in which saponin extracted from Sanguisorba officinalis is combined with vitamin E.

However, apparently thus far there has been no proposal to use an extract of a rosacea of the genus Sanguisorba officinalis for promoting pigmentation of the skin, the body hair and/or the cranial hair and/or use of the extract as a propigmentation agent.

The invention, therefore, resides in the use of at least one extract of a rosacea of the genus Sanguisorba in a cosmetic composition and/or for use in the production of a dermatological composition, the function of the extract and/or the composition being to promote the pigmentation of the skin, the body hair and/or the cranial hair.

The invention is also directed to the use of at least one extract of a rosacea of the genus Sanguisorba as a propigmentation agent and/or simulator of melanogenesis in a cosmetic composition and/or for producing a dermatological composition.

The invention furthermore is directed to a cosmetic process for pigmenting the skin, the is body hair and/or the cranial hair, which process consists in applying, to the skin, the body hair and/or the cranial hair, a composition which comprises at least one extract of a rosacea of the genus Sanguisorba.

The extract employed in the invention is advantageously an extract of Sanguisorba officinalis, with the extract preferably being prepared from the roots and/or the rhizome of the species.

Any method of extraction known to one of skill can be used to prepare the extract. Suitable methods, in particular, include extracting the starting material with an aqueous or alcoholic medium or extracting the material with an appropriate other organic solvent.

An aqueous solvent is understood as being any solvent which consists entirely or partially of water. Those which may be mentioned are, therefore, water itself, solvents which are hydroalcoholic in any proportion, or else solvents which consist of water and a compound such as propylene glycol in any proportion.

A suitable alcoholic solvent, in particular, is ethanol.

Whatever the method of preparation employed in the invention, subsequent steps which are directed to promoting preservation and/or stabilization may be employed which does not modify the nature of the extract. Thus, for example, the extract which is obtained may be lyophilized using any standard method of lyophilization. Such a procedure results in a powder which may be used directly or alternatively mixed in an appropriate solvent before being used.

Use is preferably made, according to the invention, of a dry extract of Sanguisorba officinalis root and rhizome which can be obtained in the form of a powder from MARUZEN PHARMACEUTICALS CO., LTD., Japan.

The quantity of extract contained in the composition of the invention obviously depends on the effect desired and for this reason can vary widely. Generally speaking, the extract of a rosacea of the genus Sanguisorba is present in the composition in a quantity which is effective for obtaining the desired degree of pigmentation, and advantageously in a quantity which is at least 0.002% of the total weight of the composition, for example in a quantity of 0.002 to approximately 10% by weight, preferably in a quantity of approximately 0.1% to approximately 5% by weight and, even more preferably, in a quantity of approximately 0.5% by weight.

The composition the invention is intended to be applied to the skin, the body hair and/or the cranial hair with the objective of promoting their pigmentation and/or stimulating melanogenesis, and, to this end, the composition can be present in any pharmaceutical form which is suitable for a topical application.

The composition of the invention can, therefore, be present in the form of an aqueous, hydroalcoholic or oily solution, of an oil-in-water or water-in-oil or multiple emulsion, of an aqueous or oily gel, of an anhydrous liquid, pasty or solid product, of a dispersion of oil in an aqueous phase using spherules, with it being possible for these spherules to be polymeric nanoparticles such as nanospheres and nanocapsules, or, preferably, of lipid vesicles of the ionic and/or non-ionic type.

This composition can be more or less fluid and have the appearance of a white or colored cream, of an ointment, of a milk, of a lotion, of a serum, of a paste or of a foam. It can, where appropriate, be applied to the skin, to the body hair or to the cranial hair in the form of an aerosol which also contains a propellant under pressure. It can also be present in solid form, for example in the form of a stick. It can be used as a care product and/or as a make-up product. It can alternatively be present in the form of a shampoo or a conditioner.

The composition of the invention can also, in a known manner, contain the adjuvants which are customary in the cosmetics and dermatological fields such as hydrophilic or lipophilic gelatinizing agents, hydrophilic or lipophilic active compounds, preservatives, antioxidants, solvents, perfumes, fillers, filters, pigments, odor-absorbers and coloring materials. The quantities of these various adjuvants are those which are customarily used in the fields under consideration and they represent, for example, from 0.01–20% of the total weight of the composition. Depending on their nature, these adjuvants can be introduced into the fatty phase, into the aqueous phase, into the lipid vesicles and/or into the nanoparticles.

When the composition of the invention is an emulsion, the amount of the fatty phase can range from 5–80% by weight, preferably from 5–50% by weight, based on the total weight of the composition. The oils, the emulsifiers and the coemulsifiers employed in the composition in the form of an emulsion are selected from those which are customarily employed in the field under consideration. The emulsifier and the coemulsifier are present in the composition in an amount ranging from 0.3–30% by weight, preferably from 0.5–20% by weight, based on the total weight of the composition.

Oils which can be used in the invention, and which may be mentioned, include mineral oils (vaseline oil), oils of vegetable origin such as avocado oil and soya bean oil), oils of animal origin such as lanolin, synthetic oils such as perhydrosqualene, siliconated oils such as cyclomethicone and fluorinated oils such as perfluoropolyether. Fats which can also be used include fatty alcohols such as cetyl alcohol, fatty acids and waxes such as carnauba wax and ozokerite.

Examples of emulsifiers and coemulsifiers which can be used in the invention include esters of fatty acids and polyethylene glycol such as PEG-20 stearate, and esters of fatty acids and glycerol such as glyceryl stearate.

Suitable hydrophilic gelatinizing agents include carboxyvinyl polymers such as Carbomer, acrylic copolymers such as acrylate/alkyl acrylate copolymers, polyacrylamides, polysaccharides, natural gums and clays, while suitable lipophilic gelatinizing agents include modified clays such as bentons, metallic salts of fatty acids, hydrophobic silica and polyethylenes.

Suitable active compounds which may be used include polyols such as glycerol, propylene glycol, vitamins, keratolytic agents and/or desquamating agents such as salicylic acid and its derivatives, alpha-hydroxy acids, ascorbic acid and its derivatives, anti-inflammatory agents and soothing agents, and their mixtures.

The invention also relates to a cosmetic treatment process for increasing the pigmentation of the skin, the body hair and/or the cranial hair and/or for stimulating melanogenesis, which process consists in applying, to the skin, the body hair and/or the cranial hair, a cosmetic composition which comprises at least one extract of a rosacea of the genus Sanguisorba in a cosmetically acceptable medium.

A cosmetically acceptable medium is understood as being a medium which is compatible with the skin, the mucous membranes, the nails, the body hair and the cranial hair.

Having now generally described the invention, a further understanding can be obtained by reference to certain specific examples which are provided herein for purpose of illustration only and are not intended to be limiting unless otherwise specified.

EXAMPLES

Example 1

Measuring the modulating effect on melanogenesis of an extract of Sanguisorba officinalis—coculturing keratinocytes and melanocytes 1.1. MATERIAL AND METHOD The modulating effect on the melanogenesis of a pulverulent extract of Sanguisorba officinalis obtained from MARUZEN PHARMACEUTICALS CO., LTD., Japan, was tested using the method described in FR patent application A-2 734 825 and in the article authored by R. Schmidt, P. Krien and M. Régnier: (Anal. Biochem., 235(2), 113–18, 1996).

Briefly, the method comprises the steps consisting of:

coculturing normal human melanocytes/keratinocytes in a medium containing the extract under test and a labeled melanin precursor, in this case $C^{14}$-labeled thiouracil, lysing the cells containing the melanin with protein-degrading enzymes, passing the resulting extract through an anion exchanger filter whose pore diameter is $\leq 1$ $\mu$m, and measuring the quantity of melanin bound by the filter by radioactively assaying the thiouracil.

In detail, 250,000 normal human keratinocytes and 80,000 normal human melanocytes are mixed and seeded per well of 24-well plates (Costar type) and cultured for three days in the differentiation medium. During the three following days, the culture medium is replaced daily with the defined test medium (containing, in a solvent, the extract of the invention, termed "S.O. Extract" below, at concentrations of 0.001%, 0.002%, 0.005% and 0.1%, respectively, and also 1 $\mu$Ci of $C^{14}$-labeled thiouracil/ml)

The following controls are conducted:

control culture: no extract to be tested;

positive control of melanogenesis stimulation: 1 mM tyrosine;

positive control of melanogenesis inhibition: 500 $\mu$M kojic acid.

The total radioactivity incorporated into the proteins is estimated by incorporating tritiated leucine, with this value being taken as an indicator of cytotoxicity and proliferation. The day before the sampling, tritiated leucine is added to the test medium at the rate of 1 $\mu$Ci/ml.

After incubating overnight, the cells are rinsed in phosphate buffer. The proteins are precipitated with 5% trichloroacetic acid (TCA) and washed in order to remove the free radioactivity. The proteins are incubated overnight at 40° C. with a 100 $\mu$g/ml solution of proteinase K in Tris-HCl-Triton-EDTA buffer.

50 $\mu$l of total extract are removed and transferred to a 24-well plate (Wallac), and 500 $\mu$l of liquid scintillant (Optiphase "Supermix") are added. The remainder of the extract, that is 950 $\mu$l, is filtered through a DEAE Filtermat filter. After rinsing, the filter is covered with solid "Meltilex" scintillant and transferred to a plate. The radioactivity is counted with a Wallac counter. The results are expressed as a percentage of the control in accordance with the formula:

$$\frac{(14CP/3HP) - (14CCo/3HCo)}{(14CCo/3HCo)} \times 100$$

in which:

$^{14}$CP is the mean of the $^{14}$C-thiouracil disintegrations per minute (dpm) over 3 similar wells treated with a product (P);

$^{3}$HP is the mean of the corresponding $^{3}$H-leucine dpm;

$^{14}$CP is the mean of the $^{14}$C-thiouracil disintegrations per minute (dpm) over 3 similar wells treated with a product (P);

$^{3}$HP is the mean of the corresponding $^{3}$H-leucine dpm;

$^{14}$CCo is the mean of the $^{14}$C-thiouracil dpm over 3 similar control wells (Co);

$^{3}$HCo is the mean of the corresponding $^{3}$H-leucine dpm.

The ratio of the incorporation of thiouracil to the incorporation of leucine is calculated, with this ratio expressing stimulation of melanogenesis. The products tested are then graded in dependence on their activity in accordance with the following definitions:

from 0–30% stimulation of melanin synthesis corresponds to a class 1 propigmentation agent,
from 30–60% stimulation of melanin synthesis corresponds to a class 2 propigmentation agent,
from 60–100% stimulation of melanin synthesis corresponds to a class 3 propigmentation agent, and
more than 100% stimulation of melanin synthesis corresponds to a class 4 propigmentation agent.

1.2. RESULTS

| Products | $^3$H Leu. (%/control) | $^{14}$C ThioU. (%/control) | $^{14}$C ThioU. $^3$H Leu. |
|---|---|---|---|
| 1 mM tyrosine | −3 | 42 | 46 |
| 0.1% solvent (ethanol) | 21 | −6 | −23 |
| 0.1% S.O. extract | −12 | 54 | 114 |
| 500 µM kojic acid | 11 | −18 | −26 |
| 1 mM tyrosine | 1 | 76 | 74 |
| 0.1% solvent (DMSO) | −5 | 16 | 23 |
| 0.001% S.O. extract | −5 | −3 | 1 |
| 0.002% S.O. extract | 4 | 79 | 72 |
| 0.005% S.O. extract | −9 | 635 | 705 |
| 500 µM kojic acid | −9 | −39 | −32 |

1.3. CONCLUSIONS

This product is non-cytotoxic at the concentrations tested (insignificant-variation in the incorporation of $^3$H Leu) and induces melanin synthesis from a concentration of 0.002% upwards (increase in the incorporation of: $^{14}$CThioU).

The ratio of the incorporation of thiouracil to the incorporation of leucine expresses the stimulation of melanogenesis, which can reach 700 times the control value, corresponding to a class 4 propigmentation agent.

The concentration which activates 50% of the pigmentation, or $AC_{50}$, ranges from 0.002–0.005%.

Example 2

Measuring the modulating effect on melanogenesis of the Sanguisorba officinalis extract-test on reconstructed pigmented epidermis.

2.1. MATERIAL AND METHODS

This test was conducted using a reconstructed pigmented epidermis model as described by M. Régnier and R. Schmidt in Journal of Investigative Dermatology, Vol. 102, 1994. This model has the advantage of being closer to in vivo conditions. Exactly the same mode of operation is applied as in Example 1, while detaching the epidermis before lysing the cells.

The cells employed are keratinocytes and melanocytes. After five days of immersion and seven days of emersion, the reconstructed pigmented epidermis is treated with the extract of Example 1, which is used at a concentration of 0.01% in DMSO. A 3 µl amount of solution is applied daily for five days, with two new applications being effected after the week-end interruption. The samples are removed for histology (staining with haematoxylin-eosin and with Fontana-Masson) and macrophotographs and Microflash colorimetry measurement at sixteen days of final immersion.

A fragment of reconstructed epidermis is detached from the support and treated in order to assess its activating effect on the dopa-oxidase activity of human melanocyte tyrosinase. The epidermis is brought into contact with a reducing cosubstrate (small quantities of L-dopa) in order to initiate the reaction of hydroxylating L-tyrosine to form L-dopa, which is then oxidized catalytically to dopaquinone and then to dopachrome, which is the intermediate which comes before the non-enzymic oxidation reactions which result in the formation of melanin. The reaction is read under an optical microscope.

2.2. RESULTS 2.2.1. Colorimetry

Use is made of A. CHARDON's classification (CHARDON et al., in Biological Responses to UVA Radiation, Ed. F. Urbach, 1992, Valdenmach Publ. Co. is Overland Park, Kans.) which enables epidermides to be graded from "very clear skins" to "very tanned skins" in accordance with individual typological viewpoints. The treated reconstructed epidermis is in the "tanned skins" class, whereas the control reconstructed epidermis (treated with DMSO) is in the "intermediate skins" class.

2.2.2. Tyrosinase activity

The demonstration, on a detached fragment of reconstructed epidermis, of tyrosinase activity, as revealed by means of the DOPA reaction, shows that there has been an increase in this activity in the treated cultures.

2.2.3. Quantity of melanin

Measurement of the quantity of melanin in Fontana-Masson-stained histological sections shows that the quantity of pigment has increased in the treated cultures.

2.3. CONCLUSIONS

These results confirm the strongly propigmentary effect of the Sanguisorba officinalis extract of the invention.

Example 3

Example of a composition containing at least one Sanguisorba officinalis extract.

This composition can be obtained by the customary techniques which are currently employed in cosmetics or in pharmacology. The percentages shown are percentages by weight.

| | |
|---|---|
| Powder of *Sanguisorba officinalis* extract | 0.5% |
| Glycerol | 7.0% |
| Alcohols | 5.5% |
| Carbomer | 0.3% |
| Sodium hydroxide | 0.1% |
| Preservatives | 0.6% |
| Water | qs for 100.0% |

The composition is a propigmentation gel.

The disclosure of French priority Application Number 9811154 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A method for promoting pigmentation of the skin, the body hair and/or the cranial hair, comprising:
    applying to the skin, body hair and/or cranial hair a cosmetic and/or dermatological composition comprising at least one extract of a rosacea of the genus Sanguisorba, wherein said extract is present in a form and in an amount effective to promote pigmentation of the skin, body hair and/or the cranial hair.

2. A method of stimulating melanogenesis of the skin, the body hair and/or the cranial hair, comprising:

applying to the skin, body hair and/or cranial hair a cosmetic and/or dermatological composition comprising at least one extract of a rosacea of the genus Sanguisorba, wherein said extract is present in a form and in an amount effective to stimulate melanogenesis of the skin, body hair and/or the cranial hair.

3. The method of claim 1, wherein said extract is present in a quantity of approximately 0.1% to approximately 5% by weight, based on the total weight of the composition.

4. The method of claim 2, wherein the said extract is present in a quantity of approximately 0.5% by weight, based on the total weight of the said composition.

5. The method of claim 2, wherein said extract is present in a quantity of approximately 0.1% to approximately 5% by weight, based on the total weight of the composition.

6. The method of claim 5, wherein the said extract is present in a quantity of approximately 0.5% by weight, based on the total weight of the said composition.

7. The method of claim 1, wherein said extract is an extract of Sanguisorba officinalis.

8. The method of claim 2, wherein said extract is an extract of Sanguisorba officinalis.

9. The method of claim 1, wherein said extract is an extract of the root and/or the rhizome of Sanguisorba officinalis.

10. The method of claim 2, wherein said extract is an extract of the root and/or the rhizome of Sanguisorba officinalis.

* * * * *